United States Patent
Hart et al.

(10) Patent No.: US 7,542,602 B2
(45) Date of Patent: Jun. 2, 2009

(54) DIGITAL IMAGE PROCESSING OF MEDICAL IMAGES

(75) Inventors: Jerome A. Hart, Victor, NY (US); Kathyrn E. Gruschow, Lima, NY (US); Brian M. Colwell, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 833 days.

(21) Appl. No.: 10/993,032

(22) Filed: Nov. 19, 2004

(65) Prior Publication Data

US 2006/0110019 A1    May 25, 2006

(51) Int. Cl.
*G06K 9/34* (2006.01)
(52) U.S. Cl. .................... 382/173; 382/132; 382/286
(58) Field of Classification Search ................ 382/173, 382/132, 130, 291, 100, 128, 276, 286; 378/98.12, 378/98.11, 62, 98.2; 348/646, E5.089, E5.086, 348/639, 710, E9.053, E5.073, 128; 358/464; 600/431
See application file for complete search history.

(56) References Cited

U.S. PATENT DOCUMENTS

| 5,042,077 | A  | * | 8/1991  | Burke ........................... 382/169 |
| 5,365,562 | A  | * | 11/1994 | Toker ........................... 378/37 |
| 5,644,649 | A  | * | 7/1997  | Schoeters et al. ........... 382/132 |
| 6,466,815 | B1 | * | 10/2002 | Saito et al. ................... 600/429 |
| 6,934,409 | B2 | * | 8/2005  | Ohara .......................... 382/132 |
| 7,155,043 | B2 | * | 12/2006 | Daw ............................ 382/128 |
| 7,260,249 | B2 | * | 8/2007  | Smith .......................... 382/128 |
| 2001/0024200 | A1 |   | 9/2001  | Gupta et al. |
| 2002/0136466 | A1 |   | 9/2002  | Yata et al. |
| 2005/0111746 | A1 | * | 5/2005  | Kumar et al. ................ 382/248 |

OTHER PUBLICATIONS

S.F. Millward et al., "Comparative evaluation of reporting analog films versus digital images using IRIS", Medical Imaging IV: Image Capture and Display, Feb. 1990, pp. 1-12, SPIE, vol. 1232.
M. Coristine et al., "The use of IRIS image enhancement facilities on digital images by radiologists during a clinical trial at the Ottawa Civic Hospital", Medical Imaging IV: Image Processing, SPIE, Feb. 1990, vol. 1233, pp. 426-438.

* cited by examiner

*Primary Examiner*—Sheela C Chawan

(57) ABSTRACT

A method is disclosed for processing a digital medical image using a computer with a display for viewing an input digital medical image The method includes steps of: accessing the input digital medical image; displaying the input digital medical image at a first size in an image display area of the display, the first size being smaller than the image display area; allowing a user to define a region of interest for the digital medical image displaying at least a portion of the defined region of interest in the image display area by mapping the digital medical image and at least a portion of the defined region of interest to a second, larger size within the image display area; and masking any portion of the digital image not disposed within the region of interest.

24 Claims, 4 Drawing Sheets

DIGITAL IMAGE PROCESSING OF MEDICAL IMAGES

FIELD OF THE INVENTION

The invention relates generally to the field of digital image processing, and in particular to the image processing of digital medical images.

BACKGROUND OF THE INVENTION

It is well known in the medical field to capture an x-ray image for diagnostic purposes. Once captured, the image can be distributed and/or analyzed. Some health professionals prefer to distribute and/or analyze the x-ray image in digital form. Known modalities/methods can be employed to obtain a digital medical image. For example, a medical image can be captured using x-ray film and then digitized into a digital medical image using a digitizer. In computed radiography, an image is captured on a stimulable storage phosphor medium and then converted to a digital image using CR reader. With a digital radiography system, a digital medical image can be captured directly, for example, MRIs and CTs.

Once a digital image is obtained, the image can be reviewed and/or processed for diagnostic purposes. As part of the review/diagnosis, it may be desired to focus in on a region of interest within the digital image. The ability to quickly and accurately select an area of interest is therefore important to a radiologist.

US Patent Application No. 2001/0024200 (Gupta) is directed to a method of providing a display for a graphical user interface in which a user may define a selected region of a subject image.

US Patent Application No. 2002/0136466, is directed to a radiation image displaying apparatus for displaying a target region to be diagnosed or trace-read.

U.S. Pat. No. 5,644,649 (Schoeters) is directed to a processing method in radiographic image recording systems.

An integrated radiological information system having display enhancement tools, including a Frame and Fill function, is disclosed in two papers: (1) "The use of IRIS image enhancement facilities on digital images by radiologists during a clinical trial at the Ottawa Civic Hospital", by M. Coristine et al., SPIE Proceedings, Vol. 1233, Medical Imaging IV: Image Processing, Feb. 6-8, 1990, Pages 426-438; and (2) "Comparative evaluation of reporting analog films versus digital images using IRIS", by Millward et al., SPIE Proceedings, Vol. 1232, Medical Imaging IV: Image Capture and Display, Feb. 4-5, 1990, Pages 2-12.

While such systems may have achieved certain degrees of success in their particular applications, there is a need to for a method for selecting a region of interest quickly and accurately, and displaying the selected region of interest for viewing.

SUMMARY OF THE INVENTION

An object of the present invention is to provide a method for processing a digital medical image for diagnostic purposes.

Another object of the present invention is to provide such a method which enables a user (i.e., doctor, radiologist, health professional) to select a region of interest.

Still another object of the present invention is to provide such a method which displays the selected region of interest for viewing by the user.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method of processing an input digital medical image using a computer with a display for viewing an input digital medical image. The method includes steps of: accessing the input digital medical image; displaying the input digital medical image at a first size in an image display area of the display, the first size being smaller than the image display area; allowing a user to define a region of interest for the digital medical image displaying at least a portion of the defined region of interest in the image display area by mapping the digital medical image and at least a portion of the defined region of interest to a second, larger size within the image display area; and masking any portion of the digital medical image not disposed within the region of interest. The second larger size may fill the image display area. Portions of the region of interest not within the digital medical image may be masked.

According to a second aspect of the invention, there is provided a method of processing a digital medical image using a computer with a display for viewing an input digital medical image. The method includes steps of: accessing the digital medical image; displaying the digital medical image at a first size on the display; defining an image display area on the display, the image display area being of a second size larger than the first size and the digital medical image being displayed within the image display area allowing a user to define a region of interest for the digital medical image displaying at least a portion of the defined region of interest in the image display area by mapping the digital medical image and at least a portion of the defined region of interest to a size larger than the first size within the image display area; and masking any portion of the digital image not disposed within the region of interest. Again, the second larger size may fill the image display area. Portions of the region of interest not within the digital medical image may be masked.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
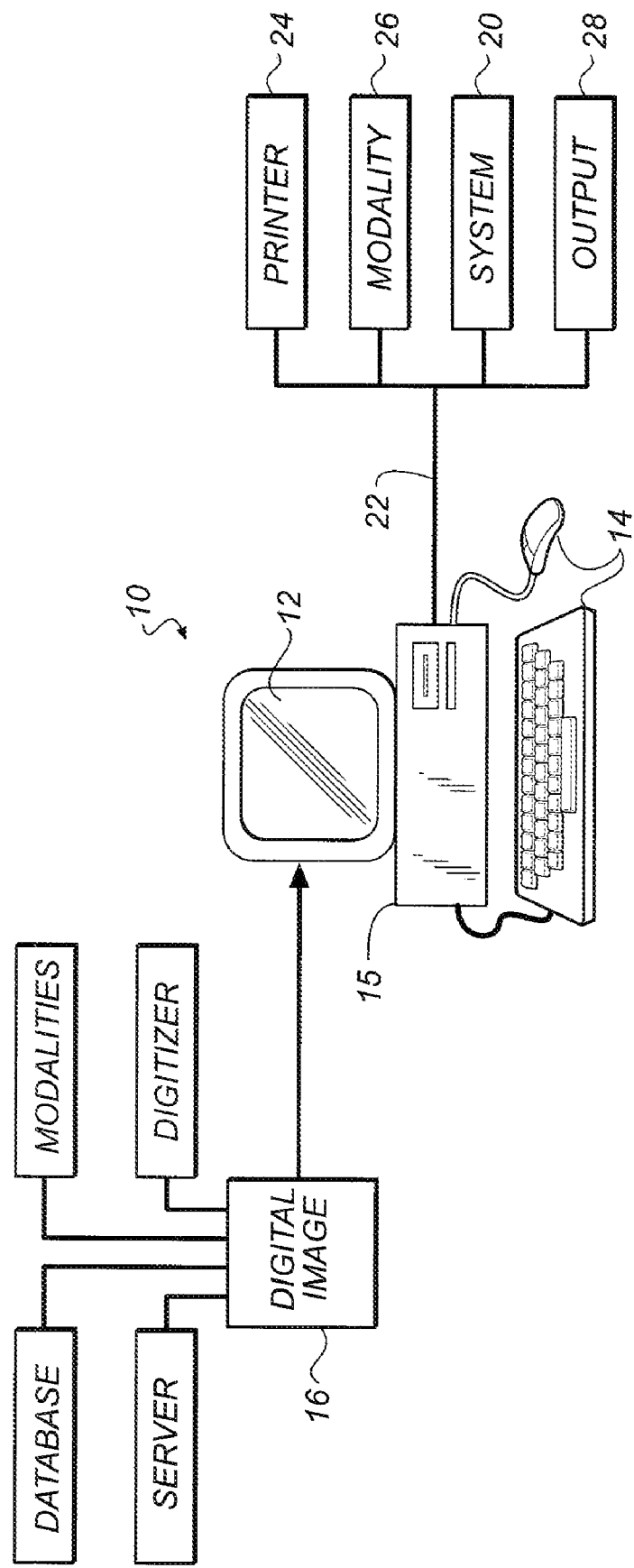
FIG. 1 shows a system which can be employed to review and process a digital medical image in accordance with the methods of the present invention.

The following is a detailed description of the preferred embodiments of the invention, reference being made to the drawings in which the same reference numerals identify the same elements of structure in each of the several figures.

A digital image can be obtained from a plurality of modalities using methods known to those skilled in the art. Once obtained, an exemplary system 10 (diagrammatically shown in FIG. 1) can be employed to review and process the digital image for diagnostic purposes in accordance with the method of the present invention. As illustrated, system 10 includes a monitor/display 12, an input device 14, and a computer or other control member 15. Input device 14 can be a keypad, mouse, joystick, or the like, as is known to those skilled in the art. Alternatively, display 12 can include a touchscreen to enable input.

System 10 accesses a digital image 16 for display on display 12. The digital image can be obtained from various sources, for example, but not limited to, a digitizer, a server, database, or one or more modalities. Once digital image 16 has been displayed/processed using system 10, the digital image (either the input digital image or a processed digital image) can be deleted, stored on a system 20, transmitted across a communication network 22, printed on a printer 24, transmitted to a modality 26, transmitted to another output device 28, or the like.

Figure 2:
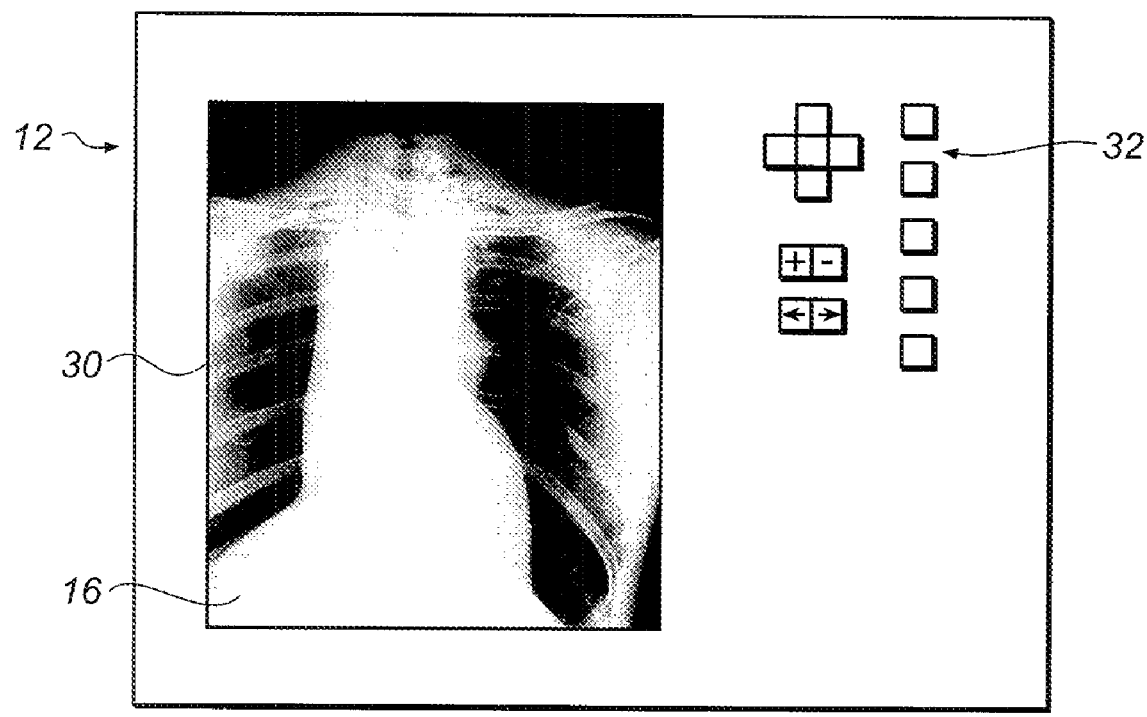
FIG. 2 shows an exemplary display displaying a digital image.

Once the digital image is accessed, it is displayed on display 12, as shown in FIG. 2. As shown, display 12 includes an image display area 30 for displaying the digital image and a control area 32 comprising viewing information as well as control members for controlling the operation of system 10 and processing of the digital image. For example, but not limited to, the viewing information might include patient information as well as zoom information. The control members might include members for manipulating the digital image displayed in image display area 30. Input device(s) 14 can also be employed to control the operation of system 10 and processing of the digital image.

When digital image 16 is accessed by system 10 and displayed in image display area 30, an individual/user (e.g., health professional, doctor, radiologist, and the like) may desire to more particularly view a particular region of interest of the digital image for diagnostic purposes. Accordingly, control area 32 or device input 14 allows for the selection of a region of interest of the digital image displayed in image display area 30 by the individual.

Figure 3:
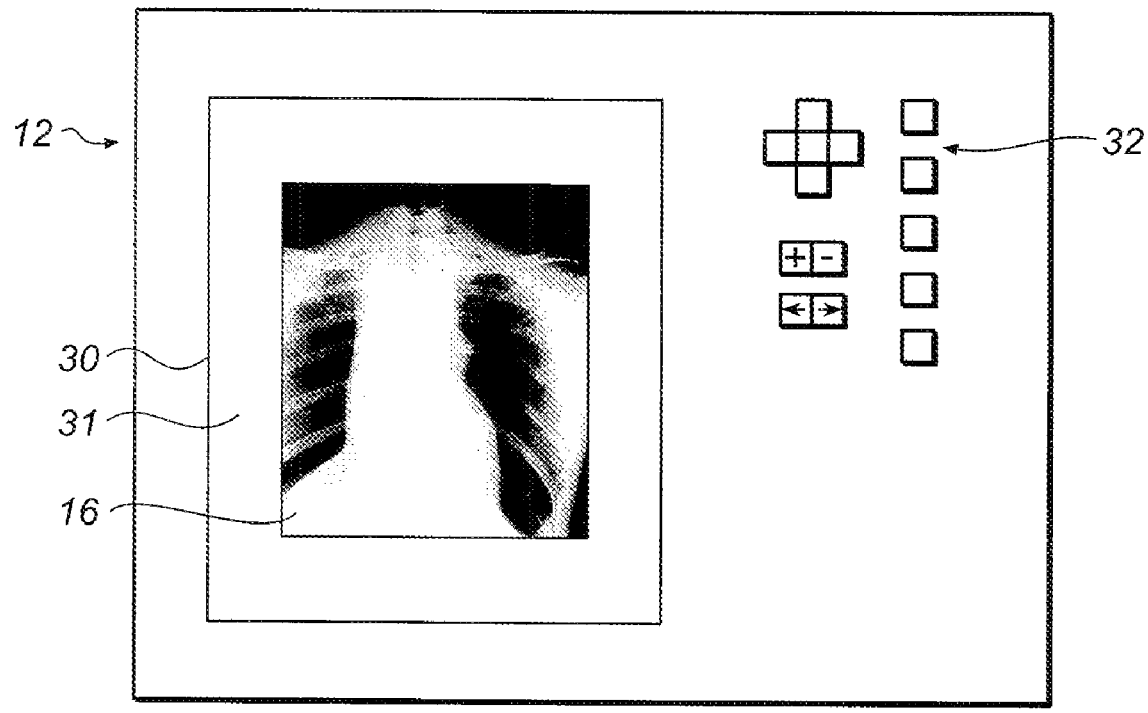
FIG. 3 shows the digital image of FIG. 2 displayed on the display in a reduced size.

Once a determination has been made to select a region of interest from the displayed digital image, digital image 16 is displayed on display 12 in a reduced size. That is, as shown in FIG. 3, image display area 30 has not changed in size relative to display 12, but digital image 16 (displayed within image display 30) has been reduced in size. As shown in FIG. 3, digital image 16 has been reduced by about 25 percent. Other size reductions can be employed, though the contents of digital image 16 need to be discernable/viewable to the individual since the individual is operating under visual control to select the region of interest.

The individual can now select/define a region of interest anywhere within image display area 30. Such a selection can be within image 16. In addition, such a selection can be made outside of image 16 but within display area 30. This area within display area 30 but outside image 16 is herein referred to as a non-image area or a border area 31.

The region of interest can be selected/defined/identified by several methods.

Figure 4:
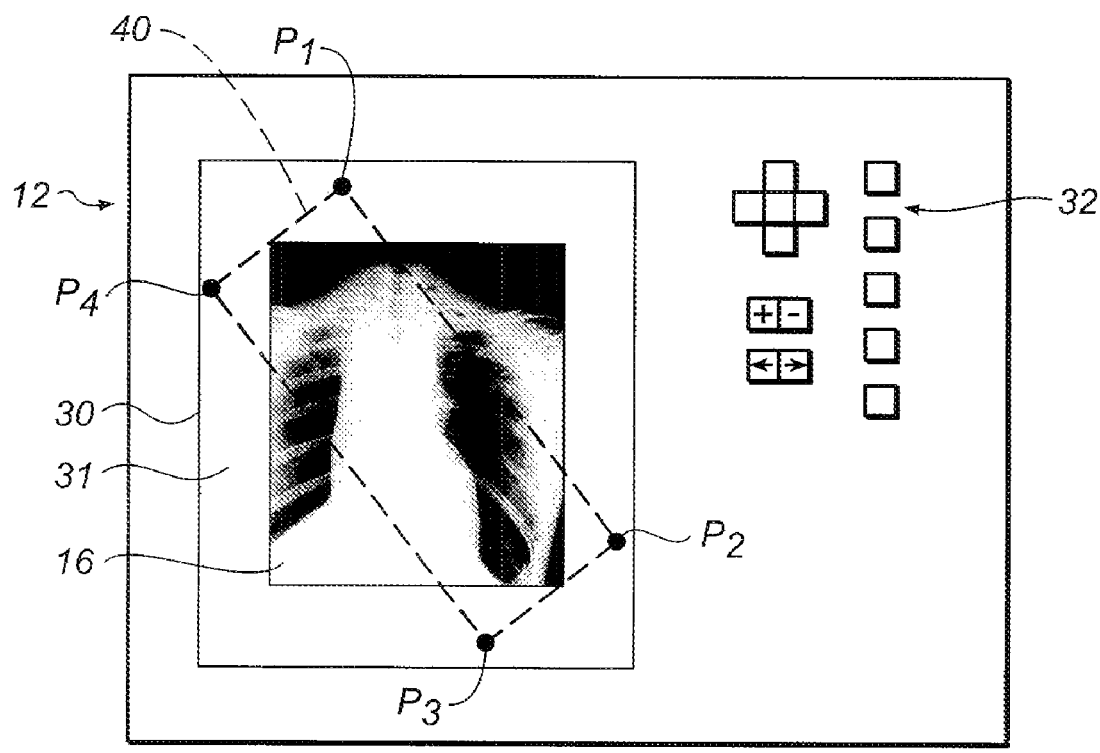
FIG. 4 shows one method of defining a region of interest in accordance with the present invention.

In one embodiment, the region of interest is selected/defined by marking corner points of the region of interest within display area 30. That is, the region of interested is defined as comprising all the image points comprised within a polygon formed by the marking of the corner points. The corner points can be marked by methods known to those skilled in the art, including but not limited to, moving a cross-hairs or a light mark within image display area 30. Acceptance/selection of a particular corner point can be noted, for example, by pressing one of the control members within control area 32 or pressing a key on keypad 14 (i.e., an input device). As shown in FIG. 4, four points (P1, P2, P3, P4) within border area 31 are marked, defining a polygon shaped region of interest 40.

In another embodiment, the region of interest can be selected/defined by marking an upper right corner and a lower left corner. The rectangle formed by these two corner points can be defined as the region of interest, wherein the image points comprised within the rectangle are the image points of interest.

Figure 5:
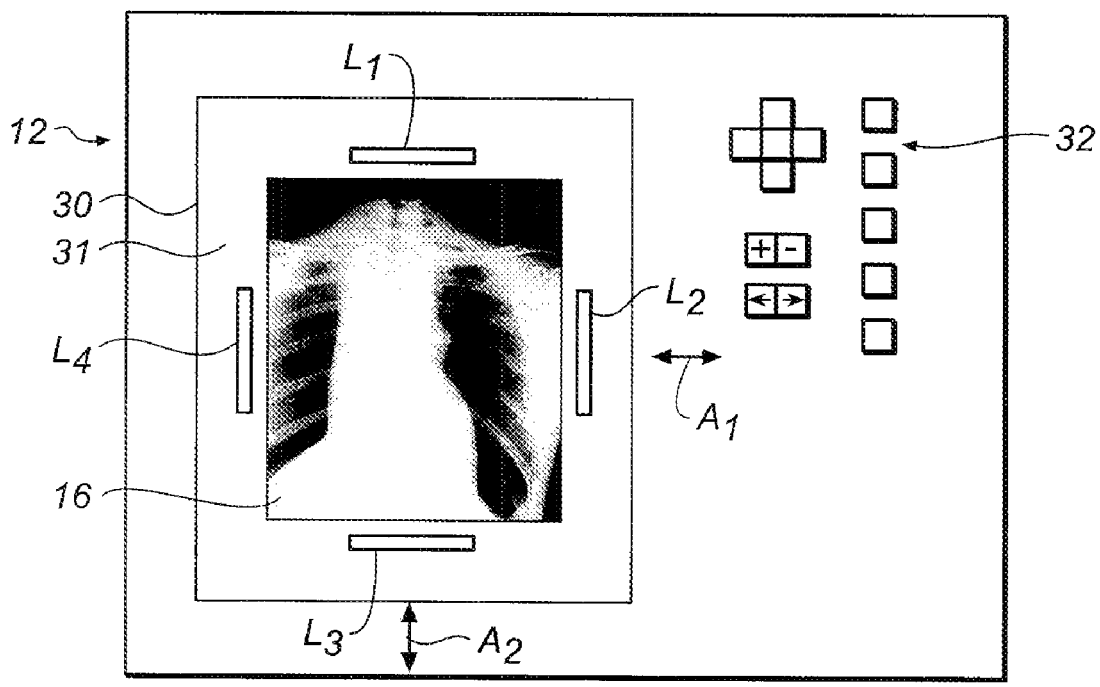
FIG. 5 shows a second method of defining a region of interest in accordance with the present invention.

In yet a further embodiment, shown in FIG. 5, four linear members (L1, L2, L3, L4), such as collimator blades, can be employed to define a polygon shaped region of interest. Linear members L2 and L4 can be moved in the direction shown by arrow A1 to define two sides of the polygon. Similarly, linear members L1 and L3 can be moved in the direction shown by arrow A2 to define two other sides of the polygon.

Other embodiments for identifying/defining a region of interest are known to those skilled in the art. For example, a center point and a radius.

As shown in FIGS. 3-5, since digital image 16 is smaller in size than image display area 30, the region of interest may comprise a portion of image display area 30 that is not within digital image 16. This can be seen in FIG. 4 wherein all four points (P1, P2, P3, P4) were selected within border area 31 (i.e., within image display area 30, but not within digital image 16). This arrangement allows the individual to more particularly control/select a particular region of interest.

Once the region of interest has been selected/defined, the region of interest can be accepted. This acceptance can be accomplished by activation of one of the control members within control area 32 or my employing one of the input devices 14, such as a left or right mouse click.

Figure 6:
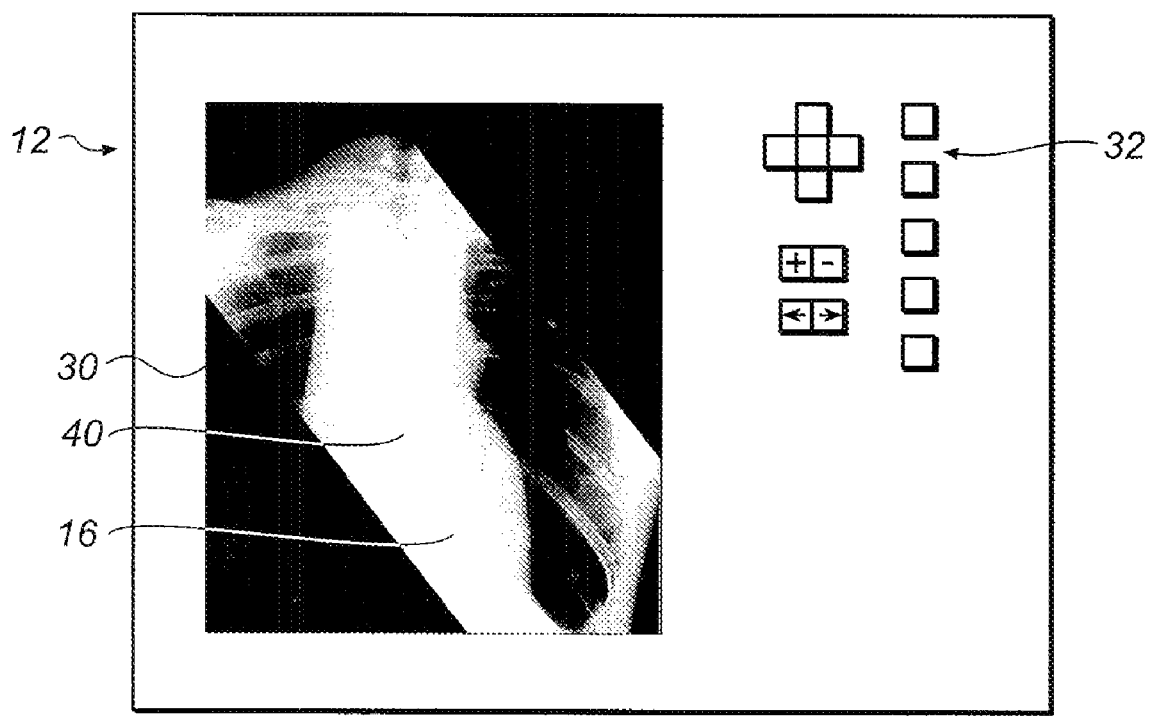
FIG. 6 shows the defined region of interest of FIG. 4 displayed on the display, but with portions of the digital medical image masked to uniform density value outside the region of interest.
Figure 7:
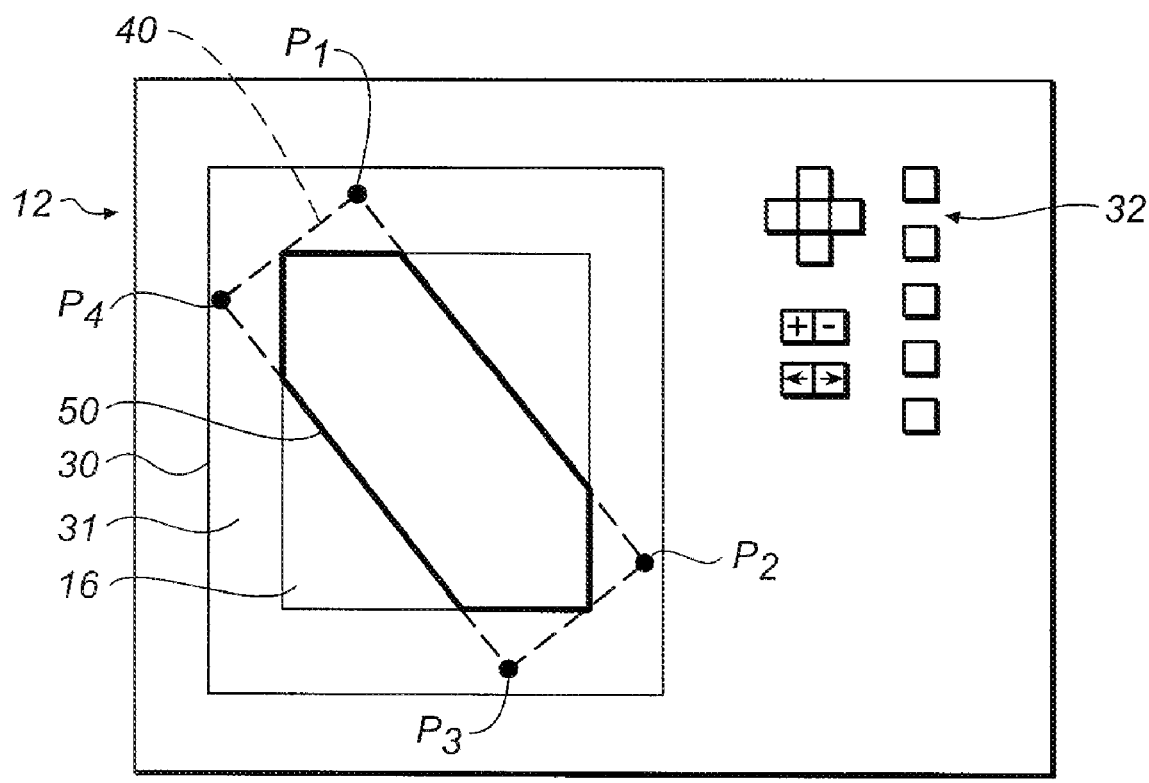
FIG. 7 shows an outline of the defined region of interest of FIG. 6.

Once the defined region of interest has been indicated/accepted as in FIG. 4, the digital medical image 16 and at least a portion of the region of interest are mapped to image display area 30. That is, the digital medical image and the portion of the region of interest with the digital medical image are increased in size so as to fill image display area 30. An example can be seen with reference to FIGS. 4 and 6. A portion of the region of interest (element 40) that was selected/defined in FIG. 4, has now been enlarged to fit within image display area 30 as seen in FIG. 6. That is, the boundary/intersection of the region of interest 40 with image 16 (shown in FIG. 7 as element 50) is enlarged in size to be mapped to display area 30.

It is noted that the defined region of interest 40 comprises portions of image 16 and portions of border area 31 (i.e., non-imaged area). The portion of image 16 within the defined region of interest is what is mapped to image display area 30.

There are portions of digital image 16 that are not within the defined region of interest that are viewable in image display area 30 when the mapping occurs. These portions of the digital image are applied with a uniform maximum density value or blackened (i.e., a density value of 3 or greater) to mask out the area that is not the region of interest, so as to reduce visual distractions for the individual making the diagnosis. That is, any portion of digital image 16 disposed within image display area 30 which is not comprised within the region of interest, is applied with a uniform maximum density value or blackened.

As seen in FIG. 4, the defined region of interest is displayed in the image display area by mapping the defined region of interest to the image display area. The portion of the defined region of interest not within the digital the image may be masked or adjusted to a uniform maximum density value, not illustrated. As seen in FIG. 6, the portion of the digital image not disposed within the region of interest also may be masked or adjusted to a uniform maximum density value.

To return to the original digital image (i.e., as shown in FIG. 2), a control member within control area 32 can be activated. Alternatively, the resulting masked image (i.e., as shown in FIG. 6) can be stored, transmitted, or printed.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method of processing a digital medical image using a computer with a display for viewing an input digital medical image, comprising steps of:
   accessing the input digital medical image;
   displaying the input digital medical image at a first size in an image display area of the display, the first size being smaller than the image display area;
   allowing a user to define a region of interest for the digital medical image;
   displaying at least a portion of the defined region of interest in the image display area by mapping the digital medical image and at least a portion of the defined region of interest to a second, larger area within the image display area; and
   masking any portion of the digital medical image not disposed within the region of interest 2. The method of claim 1, wherein the masking produces a uniform density in the portion of the digital medical image not disposed within the region of interest 3. The method of claim 1, wherein the ratio of the first size to the image display area is about 0.75.

4. The method of claim 1, wherein the step of allowing the user to define a region of interest is accomplished by the steps of:
   allowing the user to define a plurality of points; and
   defining the region of interest using the plurality of points.

5. The method of claim 1, wherein the step of allowing the user to define a region of interest is accomplished by the steps of:
   allowing the user to define a first corner point;
   allowing the user to define a second corner point; and
   defining a polygon shaped region of interest using the first and second corner points.

6. The method of claim 1, wherein the step of allowing the user to define a region of interest is accomplished by the steps of:
   allowing the user to define a center point;
   allowing the user to define a radius; and
   defining the region of interest using the center point and radius.

7. The method of claim 1, wherein the step of allowing the user to define a region of interest is accomplished by the steps of:
   providing a plurality of linear members; and
   allowing the user to move at least one of the plurality of linear members to define the defined region of interest.

8. The method of claim 1, further comprising the step of printing, storing, or transmitting the defined region of interest displayed in the image display area.

9. A method of processing a digital medical image using a computer with a display for viewing an input digital medical image, comprising steps of:
   accessing the digital medical image;
   displaying the digital medical image at a first size on the display;
   defining an image display area on the display, the image display area being of a second size larger than the first size and the digital medical image being displayed within the image display area;
   allowing a user to define a region of interest for the digital medical Image;
   displaying at least a portion of the defined region of interest in the image display area by mapping the digital medical image and at least a portion of the defined region of interest to a size larger than the first size within the image display area; and
   masking any portion of the digital medical image not disposed within the region of interest.

10. The method of claim 9, wherein the masking produces a uniform density in the portion of the digital medical image not disposed within the region of interest.

11. The method of claim 9, wherein the ratio of the first size to the second size is about 0.75.

12. The method of claim 9, wherein the step of allowing the user to define a region of interest is accomplished by the steps of:
   allowing the user to define a plurality of points; and
   defining the region of interest using the plurality of points.

13. The method of claim 9, wherein the step of allowing the user to define a region of interest is accomplished by the steps of:
   allowing the user to define a first corner point;
   allowing the user to define a second corner point; and
   defining a polygon shaped region of interest using the first and second corner points.

14. The method of claim 9, wherein the step of allowing the user to define a region of interest is accomplished by the steps of:
   allowing the user to define a center point;
   allowing the user to define a radius; and
   defining the region of interest using the center point and radius.

15. The method of claim 9, wherein the step of allowing the user to define a region of interest is accomplished by the steps of:
   providing a plurality of linear members; and
   allowing the user to move at least one of the plurality of linear members to define the defined region of interest.

16. The method of claim 9, further comprising the step of printing, storing, or transmitting the defined region of interest displayed in the image display area.

17. The method of claim 1 wherein said defined region of interest is increased in size so as to fill said image display area.

18. The method of claim 9 wherein said defined region of interest is increased in size so as to fill said image display area.

19. The method of claim 1, wherein the mapping increases the size of the digital medical image to fill the image display area.

20. The method of claim 1, further comprising a step of masking any portion of the defined region of interest not within the digital image.

21. The method of claim 2, wherein the masking produces a uniform maximum density.

22. The method of claim 9, wherein the mapping increases the size of the digital medical image to fill the image display area.

23. The method of claim 9, further comprising a step of masking any portion of the defined region of interest not within the digital image.

24. The method of claim 10, wherein the masking produces a uniform maximum density.

* * * * *